United States Patent [19]

Gallagher et al.

[11] Patent Number: 5,601,811

[45] Date of Patent: Feb. 11, 1997

[54] SUBSTANTIVE WATER-SOLUBLE CATIONIC UV-ABSORBING COMPOUNDS

[75] Inventors: Kevin F. Gallagher, Lincrost; Abel G. Pereira, Belleville, both of N.J.

[73] Assignee: Croda, Inc., Parsippany, N.J.

[21] Appl. No.: 283,575

[22] Filed: Aug. 1, 1994

[51] Int. Cl.$^6$ ....................................... A61K 7/06
[52] U.S. Cl. ................ 424/709; 424/701; 424/59; 424/401; 514/618; 514/619; 514/620
[58] Field of Search ............... 424/401, 59, 701, 424/709; 514/618, 619, 620

[56] References Cited

U.S. PATENT DOCUMENTS

| | | | |
|---|---|---|---|
| 3,879,443 | 4/1975 | Strobel | 260/472 |
| 4,256,664 | 3/1981 | Epstein et al. | 564/177 |
| 4,400,380 | 8/1983 | Ritter et al. | 424/248.5 |
| 4,734,277 | 3/1988 | Login | 424/70 |

OTHER PUBLICATIONS

Anselmi et al., *Magnetic Resonance In Chemistry*, 30, 944–9 (1992).
Saettone et al., *Internat. J. Cosmet. Sci.*, 8, 9–25 (1986).

*Primary Examiner*—Jyothsna Venkat
*Attorney, Agent, or Firm*—Lerner, David, Littenberg, Krumholz & Mentlik

[57] ABSTRACT

Substantive UV-absorbing cinnamido amine cationic quaternary salts are disclosed. Detergent and household cleaning product compositions and hair and skin personal care product compositions, as well as sunscreen and tanning lotion compositions, containing the compounds of the present invention are also described.

20 Claims, No Drawings

SUBSTANTIVE WATER-SOLUBLE CATIONIC UV-ABSORBING COMPOUNDS

BACKGROUND OF THE INVENTION

The present invention relates to substantive Ultraviolet (UV) radiation-absorbing compounds, and more particularly to water-soluble and water-dispersible cationic UV-absorbing compounds demonstrating a superior level of substantivity.

UV-absorbing compounds have found wide use in compositions such as sunscreens, tanning lotions and the like, as protective agents against sunburn or erythema. The utility of UV-absorbing compounds derive from their strong absorption of energy in the UV region of the spectrum.

Solar UV radiation having a wavelength of 290–313μ is known to produce erythema, particularly in fair-skinned individuals. Solar UV radiation of from 315–320μ to 350–400μ, on the other hand, promotes a tanning of the skin. Therefore, sunscreen and tanning compositions are preferred that remove substantially all of the burning rays, while transmitting the tanning rays. Accordingly, UV-absorbing compounds for use in such compositions must absorb at UV wavelengths known to produce erythema and at the same time absorb relatively little energy in the region of the UV spectrum known to produce skin tanning.

Commonly used UV-absorbing compounds include salicylic acid, p-aminobenzoic acid (PABA), 2-hydroxybenzophenone, 2-hydroxybenzotriazole, cinnamic acid, derivatives thereof, and the like. One drawback to these compounds is their low level of adhesion to the skin, which, in combination with high water solubility, results in their being diluted by perspiration. Constant reapplication is particularly necessary when compositions containing these compounds are used in connection with swimming activities. The failure to protect because of lack of water-resistance has remained a primary source of dissatisfaction with sunscreen products containing UV-absorbing compounds.

In the past, product formulators attempted to impart a degree of water-resistance or substantivity to compositions containing UV-absorbing compounds by formulating the compounds with water-resistant or substantive carriers. Thus, sunscreen compositions were prepared based on hydrophobic vehicles. This was undesirable for several reasons. First, the water-soluble UV-absorbing compound upon exposure to sufficient moisture would eventually be extracted, or "leached" from the water-resistant carrier. In addition, the use of such hydrophobic carriers results in a product having an undesirable oily, greasy "feel."

U.S. Pat. No. 3,879,443 discloses substantive UV-absorbing compounds in which a hydroxylamine ester of a UV-absorbing carboxylic acid is reacted with a second UV-absorbing carboxylic acid to form an acid addition salt between the amine and the second acid. U.S. Pat. No. 4,256,664 discloses cationic salicylamido amine fatty quaternary salts having enhanced skin adhesion. Nevertheless, there remains a need for UV-absorbing compounds possessing improved skin adhesion in combination with water solubility, so that a substantive product may be provided free of a greasy, oily "feel."

SUMMARY OF THE INVENTION

The present invention provides water-soluble and water-dispersible quaternary UV-absorbing compounds possessing improved skin adhesion, attributable to the presence of the quaternary group. The compounds of the present invention demonstrate the combination of water-solubility or dispersibility and skin adhesion heretofore unobtained by the prior art. This unique combination of the two properties provides a broad range of formulating options for the compounds of the present invention.

In accordance with one embodiment of the present invention, there is provided a cinnamido amine cationic quaternary salt. A preferred group of cinnamido amine quaternary salts in accordance with the present invention have the structure of Formula I:

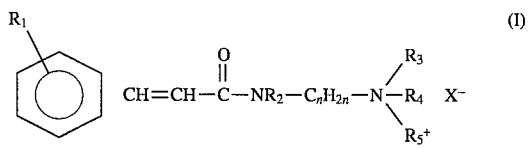

wherein $R_1$ is selected from hydrogen, halogen, alkyl groups containing up to 22 carbon atoms, alkoxy groups containing up to 22 carbon atoms, $NO_2$, $NH_2$, alkylamino groups containing up to 22 carbon atoms, OH, thioalkyl groups containing up to 22 carbon atoms and alkyl sulfonate groups containing up to 22 carbon atoms and N,N'-dialkyl alkyl amines having alkyl groups containing up to 22 carbon atoms;

$R_2$ is selected from hydrogen, —$R_6$—OH, and alkyl groups containing up to 18 carbon atoms and $R_3$ and $R_4$ are independently selected from —$R_6$—OH and alkyl groups containing up to 18 carbon atoms, wherein $R_6$ is a polyalkylene oxide containing up to 20 moles of an alkylene oxide selected from ethylene oxide, propylene oxide and mixtures thereof;

$R_5$ is selected from alkyl groups containing up to 18 carbon atoms and benzyl groups;

n is an integer between 1 and 18, inclusive; and $X^-$ is an anion.

$R_3$ or $R_4$ may also be a cinnamido alkyl group, providing compounds in accordance with the present invention having the structure, for example, of Formula II:

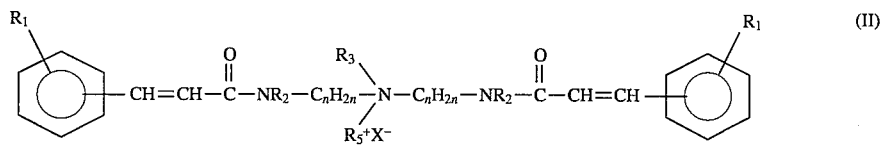

wherein $R_1$, $R_2$, $R_3$, $R_5$, n and $X^-$ are the same as described above with respect to Formula I.

As mentioned above, $R_3$ may also be a cinnamido alkyl group, and may therefore have the structure of Formula III:

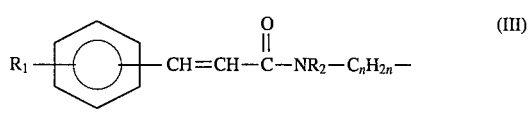

wherein n, $R_1$ and $R_2$ are the same as described above with respect to Formula I.

$R_3$ or $R_4$ may also be a quaternized cinnamido alkyl amino group, providing bis-quaternary compounds in accordance with the present invention having the structure of Formula IV:

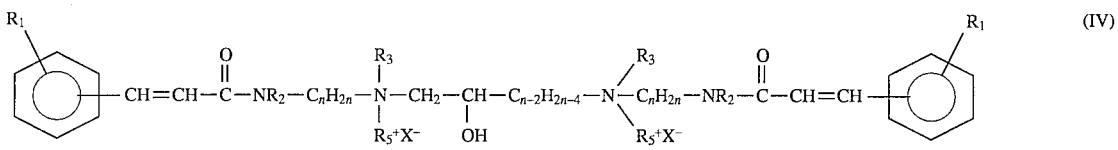

wherein $R_1$, $R_2$, $R_3$, $R_5$, n and $X^-$ are again the same as described above with respect to Formula I. One or more $R_3$ groups may also be a quaternized cinnamido alkyl amino group. $R_3$ may therefore also have the structure of Formula V:

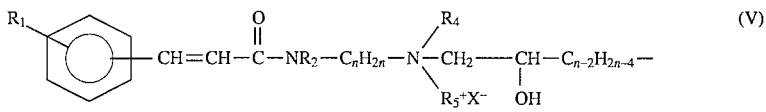

wherein $R_1$, $R_2$, $R_4$, $R_5$, n and $X^-$ have the same meaning applied throughout the within specification.

The unique combination of water-solubility or water-dispersibility and skin adhesion of the within cinnamido amine quaternary salts of the present invention has long been desired for UV-absorbing compounds to be used in sunscreens, tanning lotions and other personal care products. Therefore, in accordance with another embodiment of the present invention, aqueous solutions and dispersions of the cationic cinnamido amine quaternary salts of the present invention are provided, which may be formulated with conventional personal skin and hair care active ingredients.

Other features of the present invention will be pointed out in the following description and claims, which disclose, by way of example, the principles of the invention and the best modes which are presently contemplated for carrying them out.

DETAILED DESCRIPTION OF THE PREFERRED EMBODIMENT

The UV-absorbing compounds of the present invention are quaternary salts of cinnamic acid amido amines. The cinnamic acid amido amines are prepared by reacting a lower alkyl ester of cinnamic acid with an amino-compound having a second tertiary amino group that is subsequently quaternized.

The preferred compounds of the present invention include essentially any water-soluble or dispersible quaternary amino-amide of cinnamic acid. The object of the present invention is to obtain UV-absorption from the cinnamido moiety and a combination of water-solubility or dispersibility and substantivity from the quaternary amino group. Thus, the compounds of the present invention include essentially any quaternizable reaction product of a lower alkyl ester of cinnamic acid and an amino-compound having a second tertiary amino group, provided that the amino compound is not so hydrophobic that the resulting quaternary compound is rendered water-insoluble or non-dispersible. In addition, the amino compound should be liquid and compatible with the cinnamic acid ester at a temperature less than 200° C. and at a pressure less than 100 psi. Amino-compounds and the quaternary cinnamic acid amido amines derived therefrom meeting the foregoing requirements can be readily identified by those of ordinary skill in the art without undue experimentation.

The preferred cationic quaternary cinnamido amines in accordance with the present invention are capable of forming aqueous solutions or dispersions at levels of at least about 5% by weight of the quaternary amine per weight of water ("w/w"). Preferred quaternary amines in accordance with the present invention have a solubility or dispersibility of at least about 25% w/w and more preferably have a water solubility or dispersibility of at least 50% w/w.

Preferred quaternary amines in accordance with the present invention have the structure of Formula I. The phenyl ring of the cinnamido moiety may contain up to four ring substituents. The ring substituents, and the number utilized, should be selected so as not to render the quaternary compound water-insoluble. For purposes of the present application, water-insoluble compounds are defined as being not soluble or dispersible in water at levels above 5% w/w. As shown in Formula I, the ring is preferably unsubstituted ($R_1$ is hydrogen), or contains one substituent, $R_1$, selected from the moieties para described above for $R_1$ with respect to Formula I. Preferred ring substituents include H—, $NH_2$—, $NO_2$—, $CH_3O$—, $(CH_3)_2N$—.

Referring again to Formula I, the amido nitrogen is also preferably unsubstituted ($R_2$ is hydrogen). However, the amido nitrogen may also contain a substituent, depicted in Formula I as $R_2$, and selected from alkyl groups containing up to 18 carbon atoms and —$R_6OH$, wherein $R_6$ is the same as described above with respect to Formula I. Alkyl groups containing up to 5 carbon atoms are preferred, and a methyl group is most preferred. The polyalkylene oxide, $R_6$, preferably contains between about 1 and about 10 moles of an alkylene oxide, and more preferably contains 5 moles of an alkylene oxide. Ethylene oxide is the preferred alkylene oxide.

The quaternized tertiary nitrogen of the compounds in accordance with the present invention preferably contains two substituents, represented in Formula I, $R_3$ and $R_4$, which substituents are independently selected from alkyl groups containing up to 18 carbon atoms and —$R_6$—OH, wherein $R_6$, and the preferred species thereof and the preferred species of alkyl groups, are the same as described above with respect to $R_2$.

The compounds of the present invention are preferably quaternary salts of cinnamido alkyl amines, as shown in Formula I, in which n is an integer between 1 and 18, inclusive. Preferred compounds in accordance with the present invention are quaternary salts of cinnamido alkyl amines in which n is an integer between 2 and 12. inclusive. Most preferably, n of Formula I is 3.

The quaternary salts of the present invention are formed with conventional quaternizing agents, such as benzyl chloride or iodide, alkyl chlorides, bromides and epoxides (including alkyl chlorohydrins such as ethylene chlorohydrin and epichlorohydrin), dialkyl sulfates, and the like, wherein the alkyl groups are selected from alkyl groups containing up to 18 carbon atoms. Quaternizing agents with alkyl groups containing up to 6 carbon atoms are preferred, and methyl chloride is most preferred.

The quaternary nitrogen of compounds in accordance with the present invention will thus include a substituent derived from the quaternizing agent, such as $R_5$ of Formula I. This substituent will either be a benzyl group or an alkyl group containing up to 18 carbon atoms, which alkyl group may include a betahydroxyl group. The substituent is preferably an alkyl group containing up to 6 carbon atoms, and most preferably it is a methyl group.

As is well understood by those of ordinary skill in the art, the quaternary salts of the present invention will also include an anion derived from the quaternizing reaction. Given the quaternizing agents described above, the quaternary salts of the present invention will contain an anion, such as $X^-$ of Formula I, selected from chloride, bromide, iodide, sulfate, alkosulfate, and the like.

Preferred compounds in accordance with the present invention also include compounds of Formula I in which $R_3$, $R_4$, or both, are the cinnamido alkyl groups of Formula III. Such compounds are represented by Formula II, in which $R_1$, $R_2$, $R_3$, $R_5$, n and $X^-$, and the preferred species thereof, are the same as described above with respect to Formula I. When both $R_3$ and $R_4$ are cinnamido alkyl groups, $R_3$ will have the structure of Formula III, in which $R_1$ and n, and the preferred species thereof, are the same as described above with respect to Formula I.

Preferred compounds in accordance with the present invention also include compounds of Formula I in which $R_3$, $R_4$ or both, are the quaternized cinnamido alkyl amino groups of Formula V. Such compounds are represented by Formula IV, in which $R_1$, $R_2$, $R_3$, $R_5$, n and $X^-$, and the preferred species thereof, are the same as described above with respect to Formula I. When both $R_3$ and $R_4$ are quaternized cinnamido alkyl amino groups, more than one $R_3$ group may be present having the structure of Formula IV. In such circumstances, $R_1$, $R_2$, $R_4$, $R_5$, n and $X^-$, and the preferred species thereof, will again be the same as described above with respect to Formula I.

The compounds of the present invention are formed by reacting a lower alkyl ester of cinnamic acid with the appropriate amino compound containing a second tertiary amino group. The reaction is performed at temperatures up to 200° C. and pressures up to 100 psi. A one-half mole excess of the amino compound is utilized as the reaction solvent. Accordingly, cinnamic acid esters and amino compounds are selected that are liquid within the disclosed temperature and pressure ranges.

The temperature and pressure is selected to obtain a liquid reaction mixture. Temperatures of about 100° C. and ambient pressure are preferred.

The reaction generates a lower alkanol, corresponding to the lower alkyl ester of the cinnamic acid, which must be distilled off. Thus, lower alkyl esters of cinnamic acid must be utilized that will form alcohols capable of being distilled off at temperatures less than 200° C. and under a vacuum if necessary. Methyl esters of cinnamic acid are preferred for the ease in which the resulting methanol may be removed by distillation.

Thus, it will be appreciated that compounds having the structure of Formula I may be prepared by reacting a lower alkyl ester of cinnamic acid with a diamine having the structure of Formula VI:

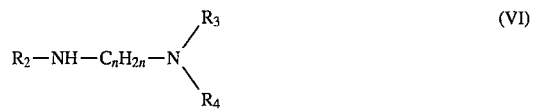

wherein n, $R_2$, $R_3$ and $R_4$, and the preferred species thereof, are the same as described above with respect to Formula I. Most preferably, n is 3, $R_2$ is hydrogen, and $R_3$ and $R_4$ are methyl groups.

The compounds of Formula I having the structure of Formula II are formed by reacting two moles of a lower alkyl ester of cinnamic acid with one mole (plus a one-half mole excess as solvent) of a dialkyl triamine having the structure of Formula VII:

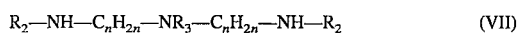

wherein n, $R_2$ and $R_3$ and the preferred species thereof, are the same as described above with respect to Formula II. Most preferably, n is 3, $R_2$ is hydrogen, and $R_3$ is a methyl group.

Condensation of the cinnamic acid ester with the amino-compound forms the cinnamido amine, which is obtained by heating the reaction mixture with stirring under the conditions described above in the presence of an effective amount of a basic catalyst such as sodium methoxide, sodium hydroxide, potassium hydroxide, and the like. From about 0.25 to about 5.0% w/w of about a 25% by weight aqueous solution of the catalyst should be employed. The preferred amount of such catalyst is 1.0% w/w.

With respect to the alkoxylated compounds of the present invention, when the amido nitrogen is polyalkoxylated, such as when $R_2$ of Formula I is —$R_6$—OH, a group, polyalkoxylation is performed on the amino-compound, such as the amino-compound of Formula VI before the amino-compound is reacted with the cinnamic acid ester to form a cinnamide. When the tertiary nitrogen is polyalkoxylated, such as when $R_3$, $R_4$, or both, are —$R_6$—OH, polyalkoxylation of this nitrogen may be performed either before or after reaction of the amino-compound with the cinnamic acid ester. Preferably, polyalkoxylation is performed after amide-formation to minimize the formation of undesirable reaction products. To first form a cinnamido amine to be polyalkoxylated, the cinnamic acid ester is reacted with an amino-compound such as the diamine of Formula VI, in which $R_3$, $R_4$, or both, are hydrogen. By carefully controlling the reaction stoichiometry, bis-amide formation can be minimized. On the other hand, it is difficult to perform the reverse reaction, in which the diamine is first polyalkoxylated, without obtaining a mixture of mono-, di-, tri- and tetra-polyalkoxylated diamines.

In any event, alkoxylation of the amido amine or amino compound can be carried out in a conventional manner. Up to about 20 moles, and preferably from about 5 to about 15 moles, and most preferably about 10 moles, of ethylene or propylene oxide, or mixtures thereof, are added to either the pure amido amine or amino-compound. The reaction between either compound and the ethylene or propylene oxide is self-catalyzing. The addition of the catalyst to the reaction mixture is not necessary.

The reaction is carried out under anhydrous conditions to avoid formation of by-products, under a temperature up to about 200° C., and preferably in the range of from about 70° C. to about 130° C. A temperature in the range of about 80° C. to about 90° C. is more preferred, although higher temperatures may be necessary, depending upon the melting point of the compound to be alkoxylated. The reaction can be carried out at atmospheric pressure, although it is preferably carried out in an autoclave at pressures of from about 10 psig to about 80 psig. As is well-understood by those of ordinary skill in the art, the amount of ethylene or propylene oxide introduced to the reaction zone, and the duration of reaction time, determines the number of moles of such components added to the amido-amine or amino compound.

Quaternization of both alkoxylated and nonalkoxylated cinnamido amines is carried out in a conventional manner. In particular, a concentrated solution of the cinnamido amine is formed in an inert solvent. The temperature of the solution will depend upon the volatility of the solvent and the quaternizing agent. Depending upon the prior reaction step performed, it may be necessary to first cool the cinnamido amine. Cooling is preferably accomplished by the use of an inert solvent having a temperature lower than the reaction mixture.

Suitable inert solvents include various lower alkanols and glycols. Lower alkanols having from one to four carbon atoms are suitable for use with the present invention, and lower alkanols having from two to three carbon atoms are preferred. Glycols having from three to eight carbon atoms are suitable for use with the present invention, while glycols having from three to six carbon atoms are preferred. Examples of suitable lower alkanols and glycols include methanol, ethanol, isopropanol, butanol, hexylene glycol, 1,3-butylene glycol, 1,2- and 1,3-propane diol, 2-methyl 1,3-propane diol, propylene glycol, diethylene glycol, and the like. The inert solvent may be mixed with between 25% and 200% w/w, and preferably, equal parts by weight, of water.

The amount of solvent added should be selected to impart a fluid viscosity to the reaction mixture, as well as to the final product, which is preferably marketed to end-users in the form of a concentrated solution or dispersion of the quaternary salt in the reaction mixture. The solids content of the reaction mixture of the cinnamido amine in the inert solvent can range from about 15% to about 90% w/w, but preferably is between about 40% and about 80% w/w, and most preferably about 65% w/w. The solids content of the quaternary salt reaction product in the reaction mixture will be slightly higher.

As previously stated, the quaternizing agents suitable for use in the present invention are essentially conventional, and are listed above, together with the preferred agents. The quaternization reaction is carried out by adding about one mole of the quaternizing agent to the reaction mixture of the cinnamido amine in the inert solvent. Temperatures suitable for this reaction range from about room temperature to about 125° C., and preferably are between about 50° C. and about 100° C. The reaction temperature will depend upon the volatility characteristics of the inert solvent and can be readily determined by those of ordinary skill in the art without undue experimentation. The resulting quaternary salt is then recovered as a concentrated solution or dispersion in the inert solvent, which serves as a vehicle or carrier for the dispersions. As noted above, the cinnamido amine quaternary salts of the present invention may be marketed in this form for many end-use applications.

Those of ordinary skill in the art will recognize that for quaternization with alkyl epoxides, the acid addition salt of the tertiary nitrogen to be quaternized must first be formed. This step is essentially conventional and is performed by adding to the reaction mixture of the cinnamido amine and the inert solvent an equimolar quantity of a neutralizing acid such as HCl, HF, HBr, $HNO_3$, $CH_3SO_3H$, $CH_3C_6H_4SO_3H$, and the like.

The bis-quaternary salts of the present invention are formed by the method described in U.S. Pat. No. 4,734,277, the disclosure of which is hereby incorporated herein by reference thereto. Essentially, the bis-quaternary compounds are formed by first partially neutralizing the reaction mixture of the cinnamido amine in the inert solvent with one of the aforementioned neutralizing acids, so that about half of the tertiary amine is neutralized, resulting in a solution in the inert solvent of equimolar concentrations of the non-neutralized tertiary amine and the tertiary amine acid addition salt. This mixture is then contacted with an alkyl chlorohydrin approximately equimolar in amount to the non-neutralized tertiary amine and tertiary amine acid addition salt, so that a reaction mixture containing equimolar quantities of all three reagents is obtained. Heating the reaction mixture as described above then forms the bis-quaternary salts of Formula IV.

Thus, it will be appreciated that compounds having the structure of Formula IV may be prepared by reacting the above-described equimolar mixture of a non-neutralized tertiary cinnamido amine and the tertiary cinnamido amine acid addition salt with an equimolar quantity of an alkyl chlorohydrin having the structure of Formula VIII:

$$H_2C\!\!-\!\!CH_2\!\!-\!\!C_{n-2}H_{2n-4}Cl \qquad \text{(VIII)}$$

wherein n, and the preferred species thereof, are the same as described above with respect to Formula I.

UV-absorbing compounds of the present invention are applied to the skin in the form of compositions such as sunscreens, tanning lotions, and the like, in which the UV-absorbing compounds are combined with a cosmetically acceptable diluent or carrier. The term "cosmetically acceptable diluent or carrier" denotes a non-toxic, non-irritating substance which when mixed with the UV-absorbing compounds of the present invention makes the compounds more suitable to be applied to the skin. The compositions can thus be solutions, lotions, liquid or solid creams, aerosols, and the like.

Sunscreen and tanning lotion compositions in accordance with the present invention are formed by admixing, dissolving or dispersing the UV-absorbing compounds of the present invention into the desired cosmetically acceptable diluent or carrier. The preferred compositions are solutions or dispersions in water. For the compounds of the present invention that are water-soluble, solutions are formed by dissolving the UV-absorbing compounds in water. Dispersions of the water-dispersible compounds of the present invention are formed by adding the compounds to water with stirring. Such compounds are self-dispersing and form aqueous dispersions without the need for additional dispersing aids.

For both solutions and dispersions, water may be combined with up to about 90% w/w, and preferably between about 25% and about 80% w/w of one or more of the above-described inert solvents, which for dispersions function as a vehicle or carrier. Other suitable inert solvents include polyethoxylated or polypropoxylated triglycerides such as the CROVOL polyalkoxylated triglycerides available from Croda, Inc. of Parsippany, N.J. and polyethoxylated or polypropoxylated fatty alcohols such as the PROCETYL polyalkoxylated fatty alcohols also available from Croda, Inc.

Lotions may be formed from an aqueous solution or dispersion of one of the UV-absorbing compounds of the present invention, with or without one or more of the above-described inert solvents, by combining the aqueous solution or dispersion with a film-forming agent. Preferred film-forming agents include film-forming proteins, film-forming polymers such as polyvinyl pyrrolidone, polyvinyl alcohols, and the like, film-forming starches and resins, and the like.

Oil-in-water and water-in-oil emulsions may also be employed as the vehicle to form lotions. The water-soluble compounds of the present invention are dissolved or dispersed in the aqueous phase of the emulsion and combined with the oil phase using a cationic emulsifier such as Behenalkonium chloride (for example, INCROQUAT B-65C), or Quaternium-26 (for example, Incroquat 26), both of which are also available from Croda, Inc. Vegetable or mineral oils are suitable for use in the oil phase, including refined mineral oil, petroleum, castor oil, sesame oil, and the like.

Conventional oil-soluble UV-absorbing compounds may also be added to the oil phase of emulsion lotions. Such UV-absorbing compounds include the p-aminobenzoates, salicylates, ferrulic acid derivatives, phenylbenzimidazole sulfonic acids, benzophenone sulfonic acids, thioctic acid derivatives, oil-soluble cinnamates, and the like. Emulsion creams may be prepared in a similar manner.

Perfumes, fragrances, anti-oxidants, preservatives, dyes, colorants, insect-repellants, fillers and other suspended particulate matter, emollients, humectants, thickeners, and the like may optionally be included in the sunscreen and tanning lotion compositions of the present invention, if desired.

The sunscreen and tanning lotion compositions of the present invention contain an effective amount of one or more of the UV-absorbing compounds of the present invention to prevent erythema. In general, an amount of about 0.5% to about 10% w/w, and preferably between about 2.5% and about 8.0% w/w, of the total composition of one or more of the UV-absorbing compounds of the present invention may be used. The compositions are applied topically every few hours as needed, in the same manner as conventional sunscreen and tanning lotion compositions.

Although the UV-absorbing compounds of the present invention are particularly useful in sunscreen and tanning lotion compositions, other important uses are indicated. The UV-absorbing compounds of the present invention may also be used to protect blonde and light-colored hair from the damaging effects of UV radiation. Accordingly, the UV-absorbing compounds of the present invention may be formulated with the above-described cosmetically acceptable diluent or carrier to provide a hair-protecting composition applied solely for this purpose.

The hair-protecting compositions of the present invention contain an effective amount of one or more of the UV-absorbing compounds of the present invention to prevent UV radiation damage to the hair. The cosmetically acceptable diluent or carrier of the hair-protecting compositions of the present invention may be formulated in such a way as to provide a composition resembling a conventional hair lotion, cream, tonic or gel. The hair-protection compositions thus formulated may be applied to the hair in the same manner as such lotions, creams, tonics or gels for protection against UV-radiation, and thereafter as desired. Cosmetically acceptable diluents or carriers used in such conventional hair care preparations may also be used in the hair-protecting compositions of the present invention.

In addition, the hair protecting compositions of the present invention may also be formulated as hair care products such as shampoos, cream rinses, hair conditioners, hair dressing preparations, neutralizing agents for permanent waving solutions and hair relaxers, hair coloring products and the like, capable of protecting hair from UV-radiation damage, for use in essentially any color hair. Likewise, an amount of the UV-absorbing compounds of the present invention effective to prevent erythema may be formulated with skin care products such as skin lotions, moisturizers, cleansing creams, liquid hand and body soaps, bath additives, and the like, as well as with cosmetic products such as lipstick, foundation, shaving preparations, and the like, to impart these products with the ability to prevent erythema.

Furthermore, the UV-absorbing compounds of the present invention can be effectively incorporated into detergent-containing products, so that repeated washing and bathing with such detergent products leaves a long-lasting substantive amount of the UV-absorbing compounds on the skin effective to prevent erythema. Thus, the UV-absorbing compounds of the present invention are also useful in detergents and other household cleaning products to impart these products with the ability to protect the skin from UV radiation. Such products are also formed by formulating an amount of the UV-absorbing compounds of the present invention effective to prevent erythema in conventional detergent and household cleaning product compositions to impart these products with the ability to prevent erythema.

Thus, detergent, household cleaning product and hair and skin protecting compositions in accordance with the present invention may be provided by formulating aqueous solutions or dispersions of the UV-absorbing compounds of the present invention with one or more active ingredients such as aqueous and oily moisturizers, film-forming agents, cationic emulsifiers, thickening agents, skin and hair conditioning agents, humectants, surfactants, emollients, theological modifiers, and the like.

Like the sunscreen and tanning lotion compositions described above, the aqueous solutions and dispersions may be formed into oil-in-water or water-in-oil emulsions. In addition to the active ingredients, the detergent, household cleaning product and hair and skin protecting compositions of the present invention may also' optionally include dyes, coloring agents, optical brighteners, perfumes, fragrances, sanitizers, antioxidants, preservatives, and the like. These additional components may be added in various amounts as is well known to those of ordinary skill in the art.

Typical detergent and household cleaning product compositions in accordance with the present invention include one or more surfactants, selected from anionic, cationic, nonionic and amphoteric detergents, alone or in combination; which are present in an amount from about 0.50% to about 25% w/w of the composition, on an active basis for each detergent present and preferably from about 1.50% to about 20% w/w. Many detergents are marketed as aqueous solutions, and those of ordinary skill in the art refer to the actual detergent content as the "active basis." Thus, 100 parts of a 20% w/w detergent solution must be utilized to add 20 parts of detergent "on an active basis." Triethanolamine, lower alkanols such as ethanol, fragrances, optical brighteners, coloring agents, sanitizers, and the like, may also be present.

Anionic, cationic, nonionic and amphoteric detergents are also used in surfactant-containing personal skin and hair care products of the present invention. With respect to the detergent and household cleaning product compositions of the present invention, as well as the hair and skin protecting products of the present invention, suitable cationic detergents include behenalkonium chloride, Quaternium-26, cetrimonium chloride, and the like. Suitable anionic detergents include sodium lauryl sulfate, sodium oleyl succinate, ammonium lauryl sulfosuccinate, sodium lauryl ether sulfate, ammonium lauryl sulfate, sodium dodecylbenzene sulfonate, triethanolamine, dodecylbenzene sulfonate, sodium N-lauroyl sarcosinate, sodium laureth sulfate, triethanolamine lauryl sulfate, and the like.

Suitable amphoteric or ampholytic detergents include N-lauryl-N'-carboxymethyl-N-(2-hydroxyethyl) ethylenediamine, cocobetaine, the Miranol compounds in U.S. Pat. Nos. 2,528,378 and 2,781,354, cocoamidopropyl hydroxysultaine, lauroampho diacetate, cocoamidopropylbetaine, and the like. Other suitable amphoteric detergents include the quaternary cycloimidates, betaines and sultaines disclosed in U.S. Pat. No. 3,964,500. Nonionic surfactants include polysorbate 20, laurylamide DEA, sucrose monococate, and the like.

Hair and skin protecting products in accordance with the present invention include one or more of the above-listed active ingredients, with, or without, a detergent. Such ingredients may also be present in an amount from about 0.5% to about 25% w/w, and preferably from about 65% to about 20% w/w.

Among the preferred emollients that may be used with the personal skin and hair care products of the present invention are the polyalkoxylated fatty alcohol diesters and triesters of aliphatic and aromatic dicarboxylic and tricarboxylic acids disclosed by U.S. Pat. No. 5,302,377, the disclosure of which is hereby incorporated herein by reference thereto. Particularly preferred are the polyalkoxylated fatty alcohol triesters of citric acid available from Croda, Inc. of Parsippany, N.J.

The hair and skin protecting and detergent and household cleaning composition of the present invention are also formed by admixing, dissolving or dispensing the UV-absorbing compounds of the present invention into the desired cosmetically acceptable diluent or carrier. The preferred compositions are solutions or dispersions in water. The compositions contain an effective amount of one or more of the UV-absorbing compounds of the present invention to prevent erythema. In general, an amount of about 0.5% to about 10% w/w, and preferably between about 2.5% and about 8.0% w/w of the total composition of one or more of the UV-absorbing compounds of the present invention may be used.

The detergents, household cleaning products, personal hair and skin care products, sunscreens and tanning lotions of the present invention are formulated utilizing techniques that are well-known in the art. Typically, the ingredients are combined with mixing and the addition of heat if necessary until a uniform, homogeneous product is formed. With respect to the emulsion products of the present invention, the water-soluble and water-insoluble ingredients are mixed together separately and combined with suitable emulsifying ingredients, typically a cationic emulsifier, to form an emulsion.

The following non-limiting examples set forth hereinbelow illustrate certain aspects of the present invention. They are not to be considered limiting as to the scope and nature of the present invention.

EXAMPLES

Example 1

Preparation Of Cinnamidopropyldimethylamine

A 1000 mL four-neck round-bottomed flask was charged with 257.29 g (1.0 mole) of methyl cinnamate, 242.71 g (1.5 moles) of dimethylaminopropylamine and 5 g of a 25% w/w aqueous solution of sodium methylate. The mixture was heated to 130° C. with stirring and allowed to react for five hours. The resulting product was then heated to 190° C. and vacuum was applied to distill off the unreacted amine until a base value of 245.75 was reached. The reaction product was then cooled to 80° C. and 213 g of a 50:50 w/w ratio mixture of water and ethanol was added and mixed until homogeneous.

The final product was a light amber liquid with a solids content of 65% and a base value of 159.6.

Example 2

Preparation Of Cinnamidopropyldimethylammonium Chloride

To a stirred pressure vessel fitted with nitrogen, vacuum, heat and cooling, and a pressurized methylchloride feed, was added 703 g (2.0 mole equivalents) of the 65% solids cinnamidopropyldimethylamine solution of Example 1. The vessel was purged three times with nitrogen and heated to 75° C. Methyl chloride addition was started and cooling and heating were used as needed to maintain the temperature between 75° C. and 80° C. Pressure was kept below 50 psi. The reaction was continued until a free amine content of less than 2.0% was achieved. The product was then cooled to 50° C. and filtered.

The product was a light amber liquid with a cinnamon odor, a chloride content of 9.1% and a pH of 5.6.

Example 3

Preparation Of Shampoo

A shampoo composition containing the cinnamidopropyldimethylammonium chloride of Example 2 was prepared in accordance with the optimum formulation set forth below. Acceptable formula variations for the preparation of such shampoos are also illustrated.

TABLE I

| INGREDIENT | RANGE % (W/W) | PREFERRED % (W/W) | OPTIMUM % (W/W) |
| --- | --- | --- | --- |
| SLES 3 mole (30%) | 5.0–50.0 | 15.0–35.0 | 25.00 |
| Crosultaine C-50 | 1.0–10.0 | 2.0–7.0 | 5.00 |
| Incromide LR | 0.5–7.5 | 1.0–5.0 | 2.00 |
| Crovol PK-70 | 0.2–4.0 | 0.5–2.5 | 1.00 |
| Cinnamidopropyl-dimethylammonium chloride | 0.5–10.0 | 1.0–5.0 | 2.00 |
| Deionized Water | 18.5–83.8 | 45.5–80.5 | 65.00 |

SLES 3 is a sodium lauryl ether sulfate anionic surfactant in water, available from Henkel, Inc. Crosultaine C-50 is a cocoamidopropyl sultane amphoteric surfactant, Incromide LR is a lauramide DEA thickener, and Crovol PK-70 is a PEG 45 palm kernel glyceride conditioner, all of which are available from Croda, Inc.

The ingredients were mixed with heating to 50° C. until a uniform homogeneous mixture was formed. The resulting mixture was then cooled to room temperature with continued mixing.

The cinnamidopropyldimethylammonium chloride was found unexpectedly to be compatible with the anionic surfactant. Typically, cationic materials form insoluble salts with anionic surfactants and precipitate out of solution.

Example 4

Hair Conditioner

A hair conditioner was prepared containing the cinnamidopropyldimethylammonium chloride of Example 2 in accordance with the optimum formulation set forth below. Acceptable formula variations for the preparation of such hair conditioners are also illustrated.

TABLE II

| INGREDIENT | RANGE % (W/W) | PREFERRED % (W/W) | OPTIMUM % (W/W) |
| --- | --- | --- | --- |
| Incroquat 26 | 0.2–4.0 | 0.5–2.5 | 1.00 |
| Incroquat Behenyl TMS | 1.0–10.0 | 2.0–7.0 | 4.50 |
| Crodacol S-70 | 0.2–4.0 | 0.5–2.5 | 1.00 |
| Cinnamidopropyl-dimethylammonium chloride | 0.5–10.0 | 1.0–5.0 | 2.00 |
| Deionized Water | 72.0–98.1 | 83.0–96.0 | 92.00 |

Incroquat 26, a quaternium 26 conditioning agent, Incroquat Behenyl TMS, a behentrimonium methosulfate conditioner/thickener in ceteryl alcohol, and Crodacol S-70, a stearyl alcohol thickener, are all available from Croda, Inc.

The resulting product possessed characteristic hair conditioning properties and formed a substantive coating of hair samples with the cinnamidopropyldimethylammonium chloride.

Performance Evaluation

A 2% w/w active aqueous solution of the cinnamidopropyldimethylammonium chloride of Example 2 was prepared and evaluated for hair substantivity using rubine dye as follows:

(1) 2.5 g bleached hair tresses were washed with 2 g of a 30% sodium lauryl ether sulfate solution and rinsed with warm tap water for one minute.

(2) The washed hair tresses were then immersed for 60 seconds in a solution of 0.5% w/w Pyrazol Bordeaux 7B dye, from Sandoz Chemicals, in deionized water pH adjusted to 2.5 with sulfuric acid.

(3) The hair tresses were then rinsed in tap water for 60 seconds and allowed to air dry. A control was produced by treating another set of hair tresses in the same manner except that only deionized water was used in Step 2.

The tresses were then visually checked for the presence of dye. The control had not picked up any dye, while the cinnamidopropyldimethylammonium chloride treated tresses were noticeably red, attributable to dye adsorption. The fact that the dye was adsorbed onto the cinnamidopropyldimethylammonium chloride treated hair tresses and not to the control tresses proves that the product is substantive to hair.

The product also proved to be a strong UV-absorber in the UV-B region. A strong molar extinction coefficient of 21,605 $cm^2$ per mole was measured at 280 nm.

As will now be readily appreciated, the present invention provides UV-absorbing cationic cinnamido amine quaternary salts possessing a unique combination of substantivity and water solubility. The desirable end-use properties of the compounds of the present invention satisfy a long-felt and heretofore unmet need for substantive, water-soluble UV-absorbing compounds.

The foregoing description of the preferred embodiment should be taken as illustrating, rather than as limiting, the present invention as defined by the claims. Numerous variations and combinations of the features described above can be utilized without departing from the present invention.

What is claimed is:

1. A composition comprising one or more active ingredients and a cinnamido alkyl amine cationic quaternary salt having the formula:

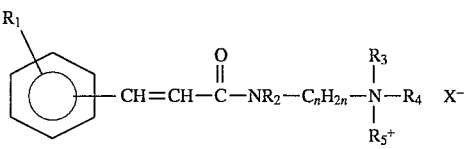

wherein $R_1$ is hydrogen;

$R_2$ is selected from the group consisting of hydrogen, —$R_6$—OH and alkyl groups containing up to 18 carbon atoms, and $R_3$ and $R_4$ are independently selected from the group consisting of —$R_6$—OH and alkyl groups containing up to 18 carbon atoms, wherein $R_6$ is a polyalkylene oxide containing up to 20 moles of an alkylene oxide selected from the group consisting of ethylene oxide, propylene oxide and mixtures thereof;

$R_5$ is selected from the group consisting of alkyl groups containing up to 18 carbon atoms and benzyl groups;

n is an integer between 1 and 18, inclusive: and x— is an anion.

2. The composition of claim 1, wherein said one or more active ingredients are selected from the group consisting of aqueous and oily moisturizers, film-forming agents, emulsifiers, thickening agents, skin and hair conditioning agents, humectants, surfactants, emollients and rheological modifiers.

3. The composition of claim 2, wherein said one or more active ingredients comprise one or more detergents selected from the group consisting of anionic detergents, cationic detergents, nonionic detergents and amphoteric detergents.

4. The composition of claim 1, wherein said one or more active ingredients are present in an amount up to about 25% w/w of said composition.

5. The composition of claim 1, wherein said cinnamide alkyl amine catonic quaternary salt is present in an amount in the range of from about 0.5% to about 10% w/w of said composition.

6. The composition of claim 1, wherein $R_2$ of said cinnamido alkyl amine cationic quaternary salt is hydrogen.

7. The composition of claim 1, wherein $R_3$, $R_4$ and $R_5$ of said cinnamido alkyl amine cationic quaternary salt are all methyl groups.

8. The composition of claim 1, wherein n of said cinnamido alkyl amine cationic quaternary salt is 3.

9. A composition comprising one or more active ingredients and a his cinnamido amine cationic quaternary salt having the formula:

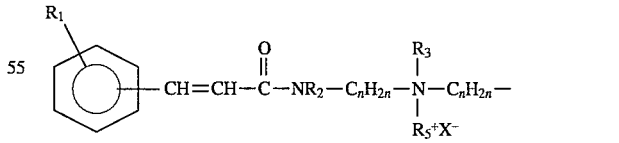

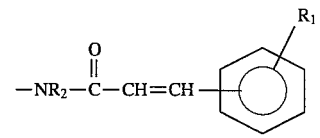

wherein each $R_1$ is independently selected from the group consisting of hydrogen, halogen, alkoxy groups containing from one up to 22 carbon atoms, $NO_2$, $NH_2$, OH and N,N'-dialkylamino groups containing from two up to 22 carbon atoms;

each $R_2$ is independently selected from the group consisting of hydrogen, —$R_6$—OH and alkyl groups containing up to 18 carbon atoms, and $R_3$ is selected from the group consisting of —$R_6$—OH, alkyl groups containing up to 18 carbon atoms and cinnamido alkyl groups having the formula:

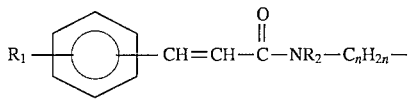

wherein $R_6$ is a polyalkylene oxide containing up to 20 moles of an alkylene oxide selected from the group consisting of ethylene oxide, propylene oxide and mixtures thereof;

$R_5$ is selected from the group consisting of alkyl groups containing up to 18 carbon atoms and benzyl groups;

n is an integer between 1 and 18, inclusive; and $X^-$ is an anion.

10. The composition of claim 9, wherein all $R_1$ groups and all $R_2$ groups are hydrogen, both $R_3$ and $R_5$ are methyl groups, and n is 3.

11. The composition of claim 1, wherein said cinnamido alkyl amine cationic quaternary salt is water-soluble or water-dispersible, and said composition comprises a solution or dispersion in water.

12. An aqueous solution or dispersion comprising water and up to about 90% w/w of a water-soluble cinnamido alkyl amine cationic quaternary salt having the formula:

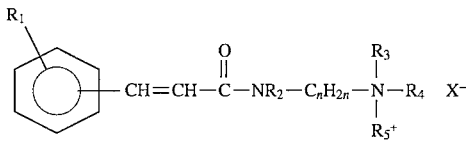

wherein $R_1$ is hydrogen;

$R_2$ is selected from the group consisting of hydrogen, —$R_6$—OH and alkyl groups containing up to 18 carbon atoms, and $R_3$ and $R_4$ are independently selected from the group consisting of —$R_6$—OH and alkyl groups containing up to 18 carbon atoms, wherein $R_6$ is a polyalkylene oxide containing up to 20 moles of an alkylene oxide selected from the group consisting of ethylene oxide, propylene oxide and mixtures thereof;

$R_5$ is selected from the group consisting of alkyl groups containing up to 18 carbon atoms and benzyl groups;

n is an integer between 1 and 18, inclusive: and x— is an anion.

13. The solution or dispersion of claim 12, further comprising an inert vehicle selected from the group consisting of lower alkanols having from 1 to 4 carbon atoms and glycols having from 3 to 8 carbon atoms, wherein said vehicle is present in a weight ratio to the water of said aqueous solution between about 1:2 and about 4:1.

14. The aqueous solution or dispersion of claim 13, comprising equal parts by weight of said water and said inert vehicle.

15. The aqueous solution or dispersion of claim 13, wherein said lower alkanols and glycols are selected from the group consisting of methanol, ethanol, isopropanol, butanol, hexylene glycol, 1,3-butylene glycol, 1,2- and 1,3-propane diol, 2-methyl 1,3-propane diol, propylene glycol and diethylene glycol.

16. The composition of claim 9, wherein said one or more active ingredients are selected from the group consisting of aqueous and oily moisturizers, film-forming agents, emulsifiers, thickening agents, skin and hair conditioning agents, humectants, surfactants, emollients and rheological modifiers.

17. The composition of claim 16, wherein said one or more active ingredients comprise one or more detergents selected from the group consisting of anionic detergents, cationic detergents, nonionic detergents and amphoteric detergents.

18. The composition of claim 9, wherein said one or more active ingredients are present in an amount up to about 25% w/w of said composition.

19. The composition of claim 9, wherein said one or more active ingredients are present in an amount in the range of from about 0.5% to about 10% w/w of said composition.

20. A composition comprising one or more active ingredients and a cinnamido amine cationic quaternary salt, wherein said quaternary salt has the formula:

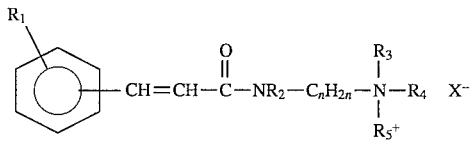

wherein $R_1$ is selected from the group consisting of halogen, $NO_2$, $NH_2$, OH and N,N'-dialkylamino groups containing from two up to 22 carbon atoms;

$R_2$ is selected from the group consisting of hydrogen, —$R_6$—OH and alkyl groups containing up to 18 carbon atoms, and $R_3$ and $R_4$ are independently selected from the group consisting of —$R_6$—OH and alkyl groups containing up to 18 carbon atoms, wherein $R_6$ is a polyalkylene oxide containing up to 20 moles of an alkylene oxide selected from the group consisting of ethylene oxide, propylene oxide and mixtures thereof;

$R_5$ is selected from the group consisting of alkyl groups containing up to 18 carbon atoms and benzyl groups;

n is an integer between 1 and 18, inclusive; and x— is an anion.

* * * * *

UNITED STATES PATENT AND TRADEMARK OFFICE
CERTIFICATE OF CORRECTION

PATENT NO. : 5,601,811
DATED : February 11, 1997
INVENTOR(S) : Gallagher et al.

It is certified that error appears in the above-identified patent and that said Letters Patent is hereby corrected as shown below:

On the cover sheet under "[75] Inventors:", "Lincrost" should read --Lincroft--.

Column 10, line 33, "theological" should read --rheological--.

Column 14, line 38, first line of claim 5, "cinnamide" should read --cinnamido--.

Column 14, line 39, second line of claim 5, "catonic" should read --cationic--.

Column 14, line 50, second line of claim 9, "his" should read --bis--.

Signed and Sealed this

Tenth Day of June, 1997

BRUCE LEHMAN

Attest:

*Attesting Officer*  *Commissioner of Patents and Trademarks*